United States Patent
Yin et al.

(10) Patent No.: US 9,042,512 B2
(45) Date of Patent: May 26, 2015

(54) MULTI-SECTOR COMPUTED TOMOGRAPHY IMAGE ACQUISITION

(71) Applicant: General Electric Company, Schenectady, NY (US)

(72) Inventors: Zhye Yin, Schenectady, NY (US); Bruno Kristiaan Bernard De Man, Clifton Park, NY (US); Jed Douglas Pack, Glenville, NY (US); Kyle Morgan Champley, Scotia, NY (US); Kai Zeng, Clifton Park, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 374 days.

(21) Appl. No.: 13/675,875

(22) Filed: Nov. 13, 2012

(65) Prior Publication Data

US 2014/0133622 A1    May 15, 2014

(51) Int. Cl.
*A61B 6/03* (2006.01)
*H05G 1/46* (2006.01)
*H05G 1/32* (2006.01)
*H05G 1/38* (2006.01)
*A61B 6/00* (2006.01)

(52) U.S. Cl.
CPC ................ *A61B 6/503* (2013.01); *A61B 6/032* (2013.01); *A61B 6/5205* (2013.01); *A61B 6/541* (2013.01)

(58) Field of Classification Search
USPC .......... 378/4, 5, 8, 15, 16, 19–21, 23–27, 39, 378/69, 87, 91, 94–96, 101, 108, 109, 114, 378/119, 143, 144, 196, 197, 210, 901; 382/131, 190, 282, 284, 294, 295; 250/362, 363.01, 363.02, 250/370.07–370.09
See application file for complete search history.

(56) References Cited

U.S. PATENT DOCUMENTS

| 6,873,675 | B2 | 3/2005 | Kurady et al. |
|---|---|---|---|
| 7,227,923 | B2 | 6/2007 | Edic et al. |
| 7,924,972 | B2 | 4/2011 | Koehler et al. |
| 2004/0264628 | A1* | 12/2004 | Besson .......................... 378/5 |
| 2011/0243419 | A1 | 10/2011 | Allmendinger et al. |

OTHER PUBLICATIONS

Hu et al., "Multislice Helical CT: Image Temporal Resolution", IEEE Transactions on Medical Imaging, vol. 19, pp. 384-390, May 2000.
Kacheliriess et al., "ECG-Correlated Image Reconstruction from Subsecond Multi-Slice Spiral CT Scans of the Heart", IEEE Transactions on Medical Imaging, vol. 19, pp. 888-901, Sep. 2000.
Flohr et al., "Heart Rate Adaptive Optimization of Spatial and Temporal Resolution for Electrocardiogram-gated Multislice Spiral CT of the Heart", Journal of Computer Assisted Tomography, vol. 25, pp. 907-923, Nov.-Dec. 2001.

(Continued)

*Primary Examiner* — Bernard E Souw
(74) *Attorney, Agent, or Firm* — Fletcher Yoder, P.C.

(57) ABSTRACT

An approach is disclosed for acquiring multi-sector computed tomography scan data. The approach includes activating an X-ray source during heartbeats of a patient to acquire projection data over a limited angular range for each heartbeat. The projection data acquired over the different is combined. An image having good temporal resolution is reconstructed using the combined projection data.

22 Claims, 8 Drawing Sheets

(56) References Cited

OTHER PUBLICATIONS

Kimdon et al., "Motion Estimation and Compensation in Dynamic Spiral CT Reconstruction", IEEE Nuclear Science Symposium Conference Record, vol. 7, pp. 4204-4206, Oct. 16-22, 2004.

Koken et al., "Aperture Weighted Cardiac Reconstruction for Cone-beam CT", Physics in Medicine and Biology, vol. 51, Jul. 21, 2006.

Tang et al., "Cardiac Imaging with Multi-sector Data Acquisition in Volumetric CT: Variation of Effective Temporal Resolution and its Potential Clinical Consequences", Medical Imaging, vol. 7258, Feb. 9, 2009.

* cited by examiner

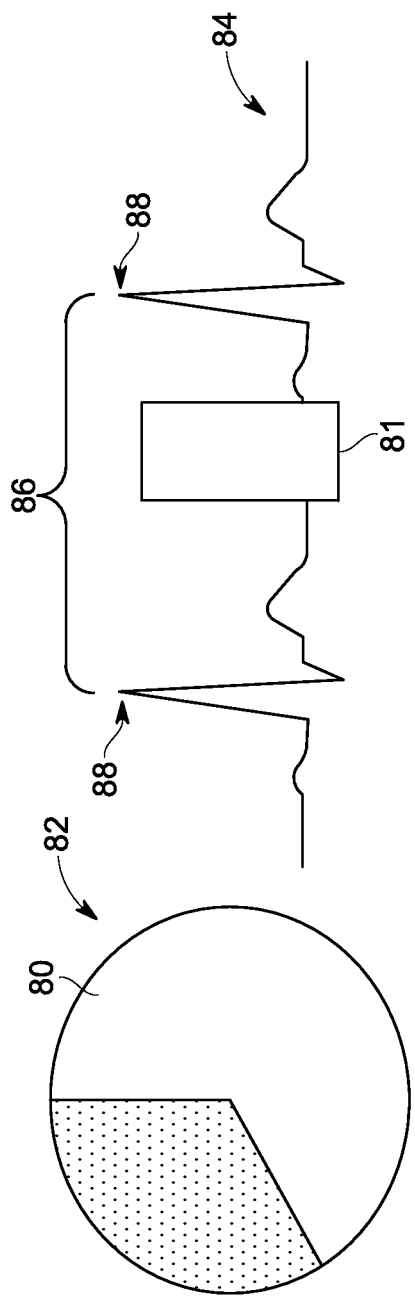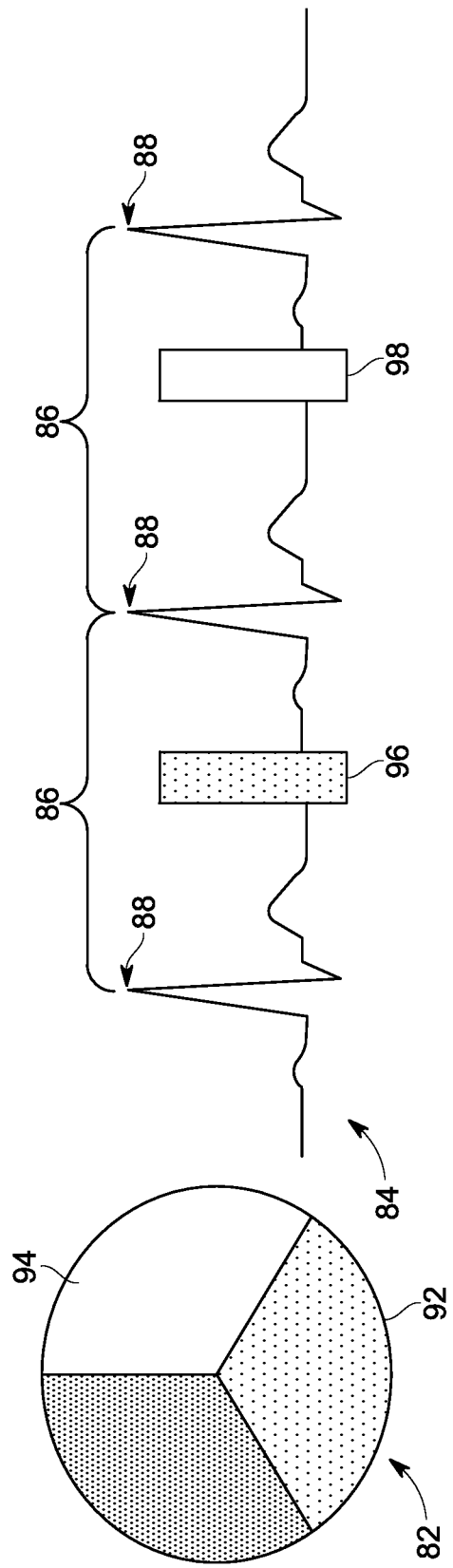
FIG. 2
FIG. 3

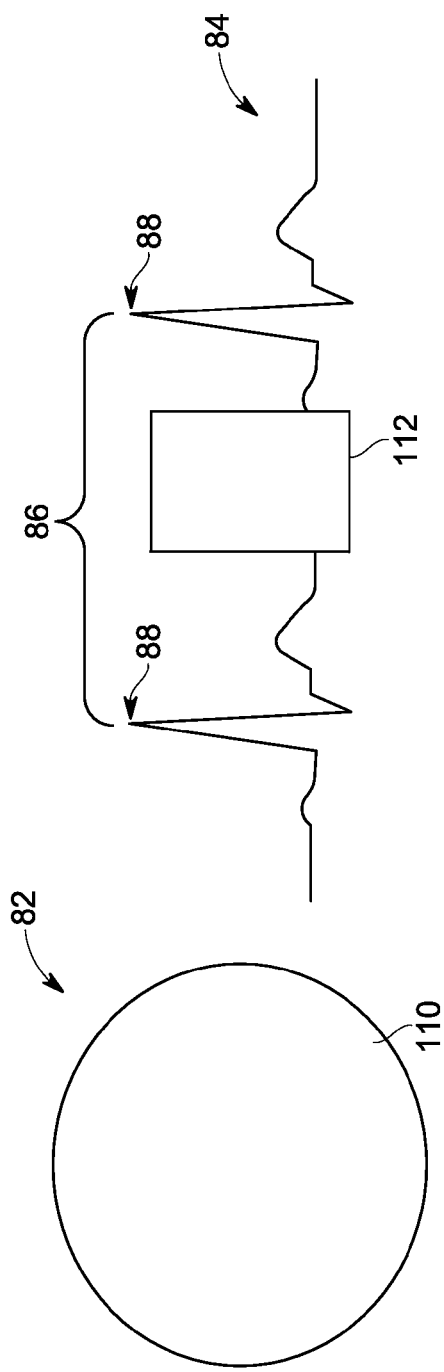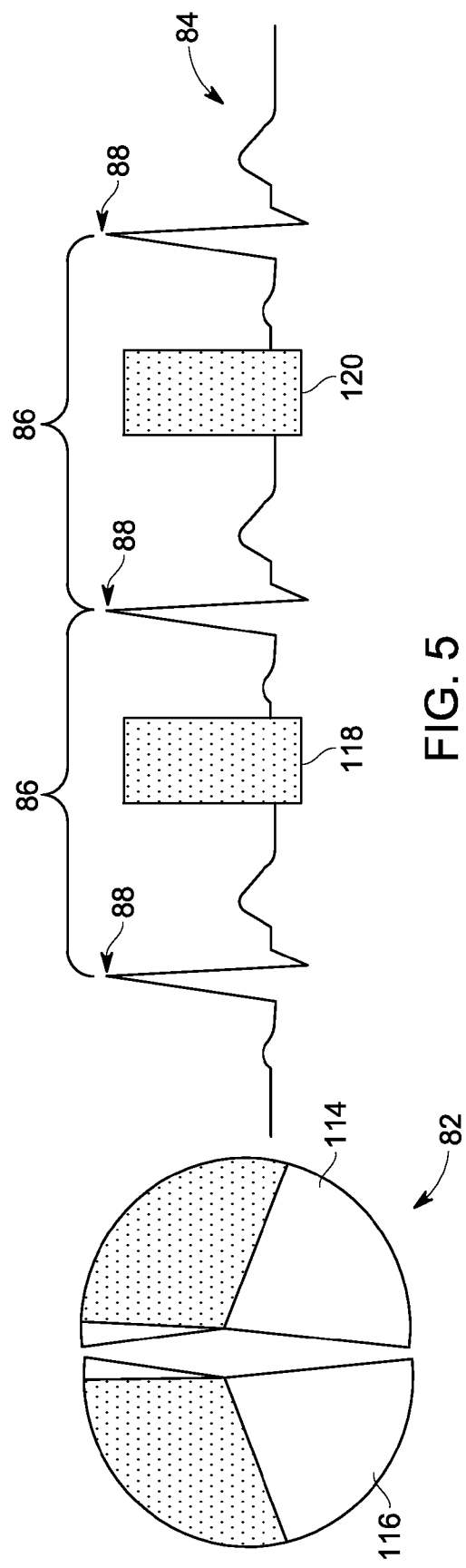
FIG. 4
FIG. 5

MULTI-SECTOR COMPUTED TOMOGRAPHY IMAGE ACQUISITION

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of X-rays through the target volume, to acquire projection data and to construct tomographic images (e.g., three-dimensional representations of the interior of the human body or of other imaged structures). However, various physical limitations or constraints on projection data acquisition may result in artifacts or other imperfections in the reconstructed image.

For example, in certain dynamic imaging contexts, such as cardiac imaging, it may be desirable to increase the temporal resolution of the imaging process to better view a portion of anatomy or a process undergoing motion. Attempts have been made to combine projection data acquired over multiple heart beats to generate images having the desired temporal resolution. However, in practice the limited coverage of conventional CT systems renders such approaches impractical due to the increased scan time involved and the presence of image artifacts associated with the boundaries of the projection data.

BRIEF DESCRIPTION

In one embodiment, a method is provided for acquiring computed tomography scan data. The method includes the act of acquiring heart cycle data for a patient undergoing imaging. An X-ray source is rotated about the patient. The X-ray source is activated during two or more heartbeats identified in the heart cycle data. The X-ray source, when activated, emits an X-ray beam that generates projection data for an imaged volume about which the X-ray source is rotating. The projection data is acquired over an angular range that is less than 180° plus a fan angle of the emitted X-ray beam during each activation of the X-ray source. The projection data acquired during the two or more heartbeats is combined to generate a substantially complete set of projection data. The substantially complete set of projection data is reconstructed to generate one or more volumetric images at a cardiac phase of interest.

In a further embodiment, a computed tomography imaging system is provided. The computed tomography imaging system comprises an X-ray source configured to emit X-rays, a detector configured to generate data in response to the X-rays emitted by the X-ray source, and a gantry upon which the X-ray source and detector rotate about an imaging volume. The computed tomography imaging system also comprises an X-ray controller configured to control activation of the X-ray source. The X-ray controller receives as an input heart cycle data and activates the X-ray source during two or more heartbeats identified in the heart cycle data. In certain embodiments, the X-ray source is activated over an angular range that is less than 180° plus a fan angle of an emitted X-ray beam during each activation of the X-ray source, though in other embodiments a full scan may be acquired on the first heart beat.

In an additional embodiment, a non-transitory, computer-readable medium is provided. The non-transitory, computer-readable medium is configured to store one or more routines executable by an imaging system. The routines, when executed, cause acts to be performed comprising: acquiring heart cycle data; rotating an X-ray source about an imaging volume; activating the X-ray source during two or more heartbeats identified in the heart cycle data, wherein the X-ray source, when activated, emits an X-ray beam that generates projection data for the imaged volume, and wherein the projection data is acquired over an angular range that is less than 180° plus a fan angle of the emitted X-ray beam during each activation of the X-ray source; combining the projection data; and reconstructing the combined projection data to generate one or more volumetric images.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 2 depicts a half-scan acquisition in the context of a heartbeat, in accordance with aspects of the present disclosure;

FIG. 3 depicts a multi-sector acquisition in the context of a series of heartbeats, in accordance with aspects of the present disclosure;

FIG. 4 depicts a full-scan acquisition in the context of a heartbeat, in accordance with aspects of the present disclosure;

FIG. 5 depicts a further multi-sector acquisition in the context of a series of heartbeats, in accordance with aspects of the present disclosure;

DETAILED DESCRIPTION

In the context of dynamic image acquisition/reconstruction it may be useful to reconstruct images having suitable temporal resolution. For instance, in the case of cardiac computed tomography (CT), the better the temporal resolution, the better the ability of the reviewer to obtain images that "freeze" the motion of the heart at a particular time. With increased temporal resolution, the reviewer is better able to obtain images that having reduced or no motion effects or artifacts attributable to the underlying motion of the heart, and is thus better able to view the heart as it appears at particular times. As will be appreciated, cardiac imaging is only one example of an imaging context where the underlying imaged region undergoes motion. Other medical and non-medical imaging contexts may also benefit from improved temporal resolution of the associated imaging process.

As discussed herein one or more approaches are described that are used to improve temporal resolution in a CT image acquisition process. Though cardiac imaging is generally described herein to provide a useful example, it should be appreciated that such examples are merely offered to facilitate explanation and are not intended to be limiting. Indeed, the algorithms and acquisition approaches discussed herein may be used in other dynamic imaging contexts and with other imaging protocols to improve temporal resolution of the image acquisition.

Figure 1:
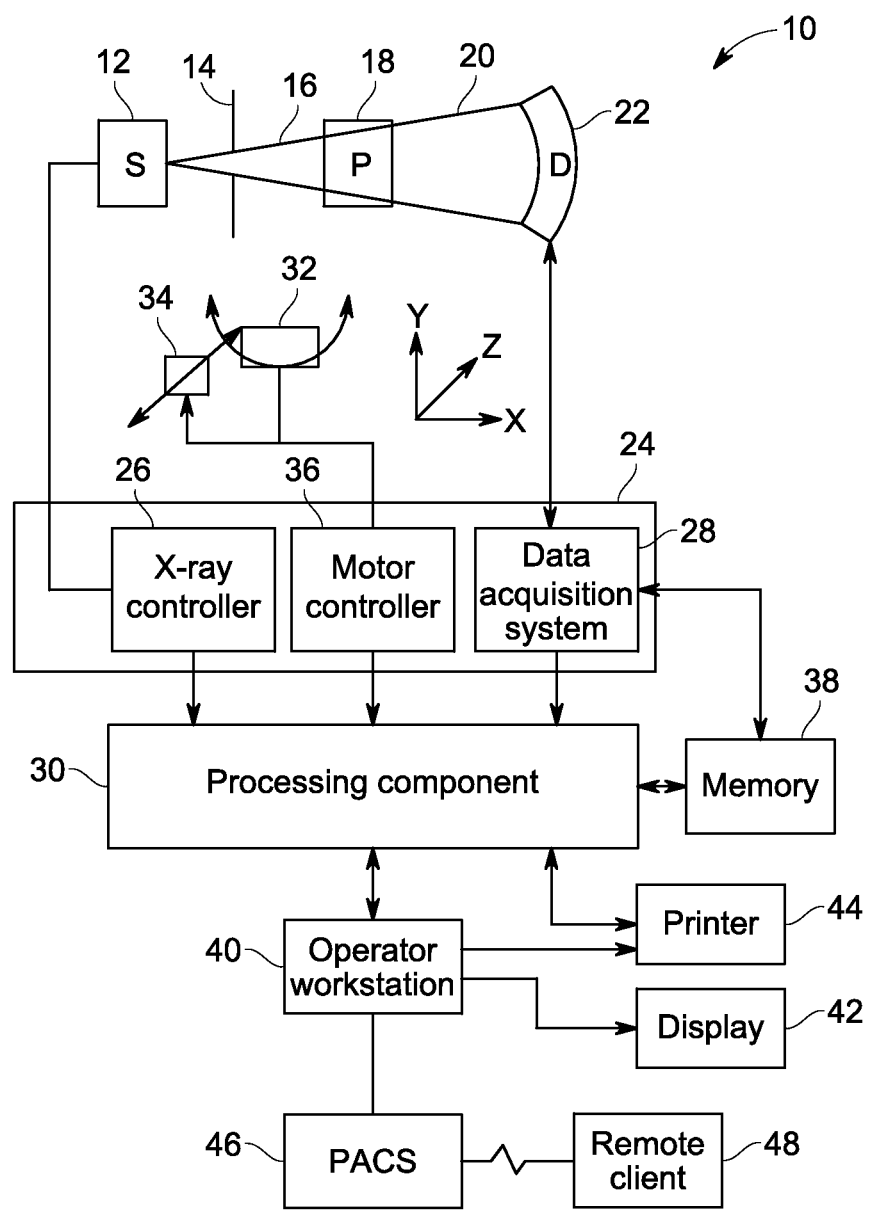
FIG. 1 is a diagrammatical view of a CT imaging system for use in producing images in accordance with aspects of the present disclosure.

With this in mind, an example of a computer tomography (CT) imaging system 10 designed to acquire X-ray attenuation data at a variety of views around a patient (or other subject or object of interest) and suitable for tomographic reconstruction is provided in FIG. 1. In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical or other images.

The collimator 14 permits X-rays 16 to pass into a region in which a patient 18, is positioned. In the depicted example, the X-rays 16 are collimated to be a cone-shaped beam, i.e., a cone-beam, that passes through the imaged volume. A portion of the X-ray radiation 20 passes through or around the patient 18 (or other subject of interest) and impacts a detector array, represented generally at reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x,y-plane about the patient. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that X-ray attenuation data may be obtained at a variety of views relative to the subject. In the present context, system controller 24 may also includes signal processing circuitry, associated memory circuitry for storing programs and routines executed by the computer (such as routines for executing image acquisition and processing techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image acquisition and/or reconstruction, as described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

As noted above, the acquisition of projection data using an imaging system, such as the depicted CT imaging system 10, may be subject to various imperfections due to motion that occurs within the imaged volume. In certain approaches involving conventional CT imaging systems having 40 mm coverage, a half scan which acquires angular views of 180°+α fan angle (a) may be employed for various gated cardiac acquisitions. For example, turning to FIG. 2, a scan range 80, corresponding to 180°+α is depicted in the context of a radial scan representation 82, is depicted as representing a data acquisition within an imaging window 81 of a heart cycle (i.e., electrocardiogram (ECG) trace 84) of a patient. In the depicted example, the depicted scan occurs within a single heart beat or cycle 86 of the patient, denoted as occurring within window 81 between the r-r peaks 88 of the ECG trace 84. In particular, FIG. 2 depicts what may be characterized as a single-sector acquisition in the present context and discussion.

Conversely, FIG. 3 depicts what may be characterized as a multi-sector acquisition in which the half scan view range is split into two or more scan or view ranges 92, 94 that are respectively acquired in different heart cycles 86, e.g., at windows 96 and 98 respectively. As used herein, a sector (in the context of a multi-sector acquisition) is a scan or view range that is less than 180°+α (e.g., 35°, 45°, 65°, 75°, 90°, 120°, and so forth). As will be appreciated, with respect to a multi-sector acquisition, depending on the gantry offset between two sectors, the lengths or view ranges 92, 94 of the respective sectors may differ or may be substantially identical. Likewise, though depicted as non-overlapping and adjacent in FIG. 3 for simplicity, the respective scan ranges 92 and 94 acquired at respective acquisition windows 96 and 98 may or may not overlap and may or may not be adjacent, depending on the heart rate of the patient and the gantry speed of the imaging system.

Since the view ranges 92, 94 for each cycle (e.g., heartbeat) of the multi-sector acquisition are smaller (i.e., of shorter duration and/or of more limited angular range) than the view range 80 associated with the single-sector acquisition, resulting images from the multi-sector acquisition may have better temporal characteristics and less motion artifacts compared to the images generated using the single-sector acquisition. However, since the start angle of second sector (e.g., scan range 92) is determined by heart rate and gantry rotation speed, conventional multi-sector acquisition may result in an unfavorable situation where one cardiac cycle dominates the subsequent cycles and thus the additional scans don't provide the desired temporal benefit.

While the preceding examples of single-sector and multi-sector acquisitions of FIGS. 2 and 3 generally relate to conventional CT imaging systems having 40 mm of scan coverage, CT imaging systems 10 providing wide coverage (i.e., coverage>40 mm) are available and may allow for alternative approaches, as discussed herein. Turning to FIG. 4, cone-beam reconstruction approaches that provide wide coverage (i.e., coverage in the z direction>40 mm) may employ a full scan 110, i.e. 360° (as opposed to 180°+a) to minimize or reduce cone-beam artifacts. In such an implementation, the full scan 110 may correspond to acquiring data at a window 112 within the cardiac cycle. A full scan view range can also be split into two or more sectors (e.g., scan ranges 114, 116) and be acquired in different heart cycles 86, such as at separate windows 118, 120, as shown in FIG. 5.

With the foregoing in mind, in certain multi-sector acquisition implementations discussed herein, the acquisition process is modified or adjusted in view of data which has already been acquired and/or data which is still needed to make the acquired data more complete. Certain of these implementations are performed using a wide coverage CT system (such as a cone-beam system) with coverage greater than 40 mm.

By way of example, in a cardiac implementation where a contrast agent is administered to the patient undergoing imaging, over a time interval when the level of contrast is high the X-ray source 12 may be pulsed for a limited duration once per heartbeat near a target phase window. In one such implementation, where the contrast bolus lasts approximately 16 seconds, an image acquisition scan might acquire approximately 16 sectors worth of data at 60 heartbeats per minute (bpm).

Figure 6:
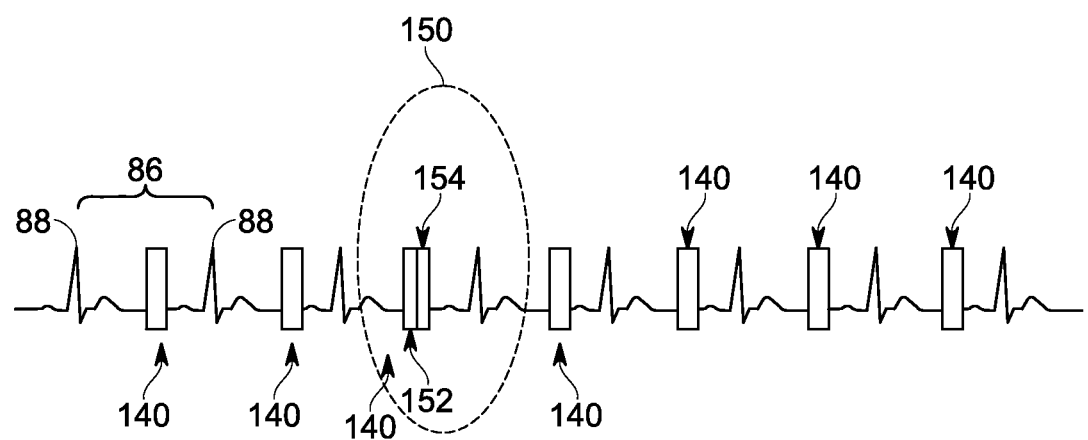
FIG. 6 depicts a multi-sector acquisition in the context of a series of heartbeats, in accordance with aspects of the present disclosure.

In an example of such an embodiment, depicted in FIG. 6, the duration of the pulsed X-ray emissions could be short (for example, covering 90° or less of a gantry rotation) and the operating current (i.e., mA) associated with each pulse could be independently and separately controlled or specified for each pulse. That is, each X-ray pulse, corresponding in time to the depicted data acquisition windows 140 in FIG. 6) may have a different associated mA (generally characterized as the intensity associated with the pulse) and duration (which corresponds to view range over which data is acquired). The starting and ending view of each pulse may vary, depending on when a respective window 140 begins and, in some embodiments, the extent to which the view range corresponding to the respective window 140 has already been sampled. In certain implementations, approximately 90° of data from each heartbeat may be employed in the image reconstruction process, though more or less data associated with each heartbeat may be employed, depending on the factors considered.

In one implementation, the duration and/or mA of each pulse may be determined based upon how much total mA has already been used for a scan or view range of interest and/or based on the position of the source 12 with respect to sensitive organs (such as the breasts). In this manner, patient exposure may be controlled, taking into account anatomic considerations, cumulated dose for a scan or view range, and/or the sufficiency of data already acquired for a scan or view range during an examination.

By way of example, if the scan range around the center-view (i.e., the center-view associated with a data acquisition window 140) was under-sampled at the time of an X-ray pulse, as compared to other sectors of the scan, the mA for that heartbeat could be increased to a compensatory degree to address the under-sampled state of the present view range. Conversely, if the scan range around the center-view was over-sampled or otherwise sufficiently sampled at the time of an X-ray pulse, the mA for that heartbeat could be decreased as additional data in that scan range is not needed.

As with the mA, the amount of data used from each heartbeat may also be adjusted based on various considerations. For example, if the angular sector from 50°-100° had already been scanned several times (or was otherwise fully sampled), but the sector from 0° to 50° had only been scanned once (or, more generally, had been scanned less often than the fully sampled range) and the next centerview was going to be at 50°, an upcoming pulse might be configured so to fill in the region from 0° to 50° (instead of 5° to 95° or 0° to 90°). An example of such an X-ray pulse configuration is depicted in FIG. 6 at the scan interval encompassed by dotted circle 150. In this depicted example, a modulated pulse 152 is depicted that spans a limited portion (e.g., 0° to 50°) of a greater angular range (e.g., a 90° range) such that projection data is acquired only for the limited angular range in response to the modulated pulse 152. The projection data associated with the remainder 154 of the greater angular range is acquired during previous X-ray pulses in such an example and is thus not acquired as part of the depicted heartbeat.

Figure 7:
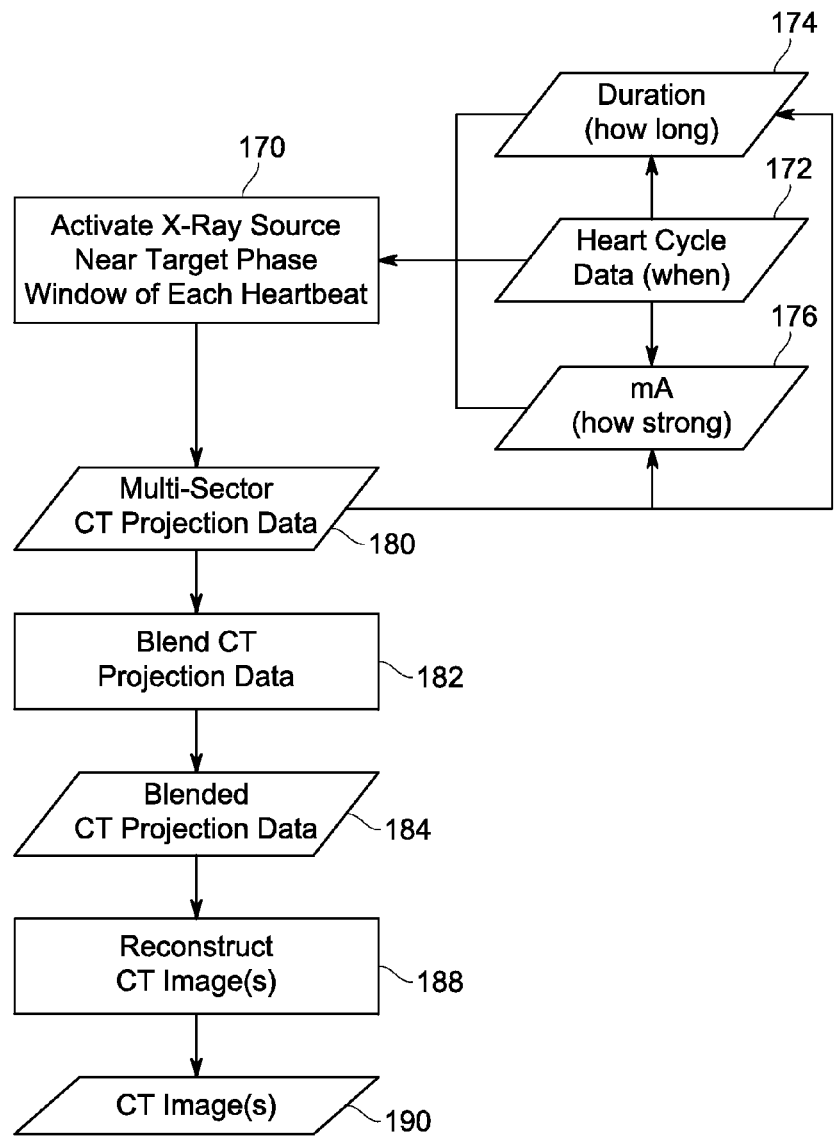
FIG. 7 depicts a process flow diagram of steps performed in a computed tomography data acquisition, in accordance with aspects of the present disclosure.

With the foregoing examples in mind, FIG. 7 depicts control flow logic describing steps associated with one implementation of a CT data acquisition as discussed herein. In this example, an X-ray source 12 is activated (block 170) within a target phase window for each heartbeat of a patient undergoing imaging. In certain embodiments, the X-ray source 12 is suitable for emitting X-rays in a wide-coverage area (i.e., a coverage area greater than 40 mm), such as a cone-beam.

The activation 170 of the X-ray source may be controlled based on a variety of factors including, but not limited to, the heart cycle data 172 associated with the patient undergoing imaging, duration determinations 174 made for each X-ray source activation (such as by X-ray controller 26 or system controller 24), and mA determinations 176 made for each X-ray source activation (such as by X-ray controller 26 or system controller 24). In these examples, the heart cycle data 172 may be derived from various suitable sources, such as an ECG system, image data, or other systems suitable for determining cardiac motion. In the depicted example, X-ray pulse duration determinations 174 may be based on one or both of the heart cycle data 172 as well as the multi-sector projection data 180 acquired prior to a present pulse for which the duration is being determined. Similarly, X-ray pulse mA determinations 176 may be based on one or both of the heart cycle data 172 as well as the multi-sector projection data 180 acquired prior to the present pulse for which the mA is being determined.

The acquired multi-sector projection data 180 may be blended or otherwise combined (block 182), as discussed in greater detail below, so as to generate a complete data set 184 with respect to the cardiac phase of interest. This data set 184 may be reconstructed (block 188) to generate one or more CT images 190 at the phase of interest for review.

Figure 8:
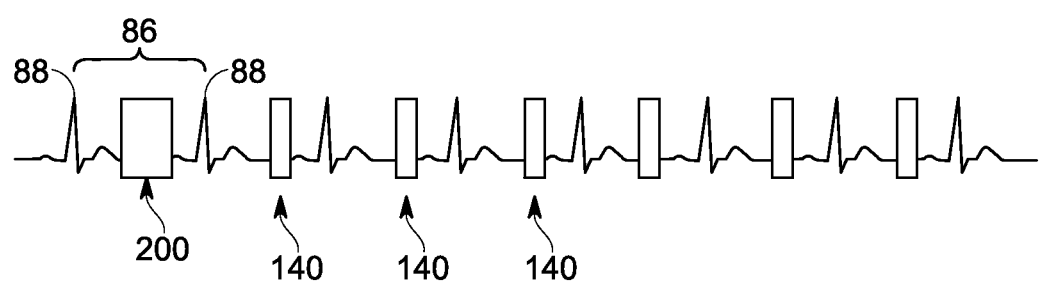
FIG. 8 depicts a multi-sector acquisition in the context of a series of heartbeats, in accordance with aspects of the present disclosure.

Turning to FIG. 8, in an alternate embodiment, a full 360° view range 200 of data is initially acquired and data acquisitions at subsequent windows 140 are acquired using gated acquisitions in which limited sectors of data (e.g., view ranges less than 180°+a, such as view ranges of 90° or less) are acquired. The initial 360° view range scan 200 provides sufficient data to reconstruct single sector images, as discussed above. Therefore, the subsequent limited sector scans at windows 140 allow acquisition of projection data to provide data redundancy in angular sectors of interest. As the subsequent limited sector scans at windows 140 provide data that is redundant to that acquired in the full scan 200 acquired at the outset, data acquisition can cease when the angular sectors of interest have been covered completely, taking into account the data acquired in the full scan 200, such as after each view has been sampled twice.

In one implementation, the initial full 360° scan 200 may be performed at a low mA. Subsequent limited sector scans performed at windows 140 may be used to supplement the 360° initial scan 200. For example, the subsequent limited sector scans may be performed at higher mA than the initial full scan 200, such as in instances where the scan range is under-sampled relative to other views that have been sampled. For example, if a scan range corresponding to an upcoming window 140 has been sampled twice during an imaging session, but other scan ranges have been sampled more than twice, the mA of the X-ray emissions during the upcoming window 140 may be increased to compensate for the under-sampling of the upcoming scan range.

Further, to the extent that the X-ray source 12 is capable of modulating or otherwise adjusting tube current, the mA of the X-ray emissions may also be modulated or changed during a pulse delivered during a window 140. In one implementation, as the scan of the patient concludes due to contrast agent dissipating within the imaged volume, steps may be taken to acquire projection data still needed for completeness, such as by increasing mA of all or part of a pulse, as discussed above, and/or by extending a data acquisition window 140 to acquire any projection data still needed to substantially complete acquisition over a 360° range.

Figure 9:
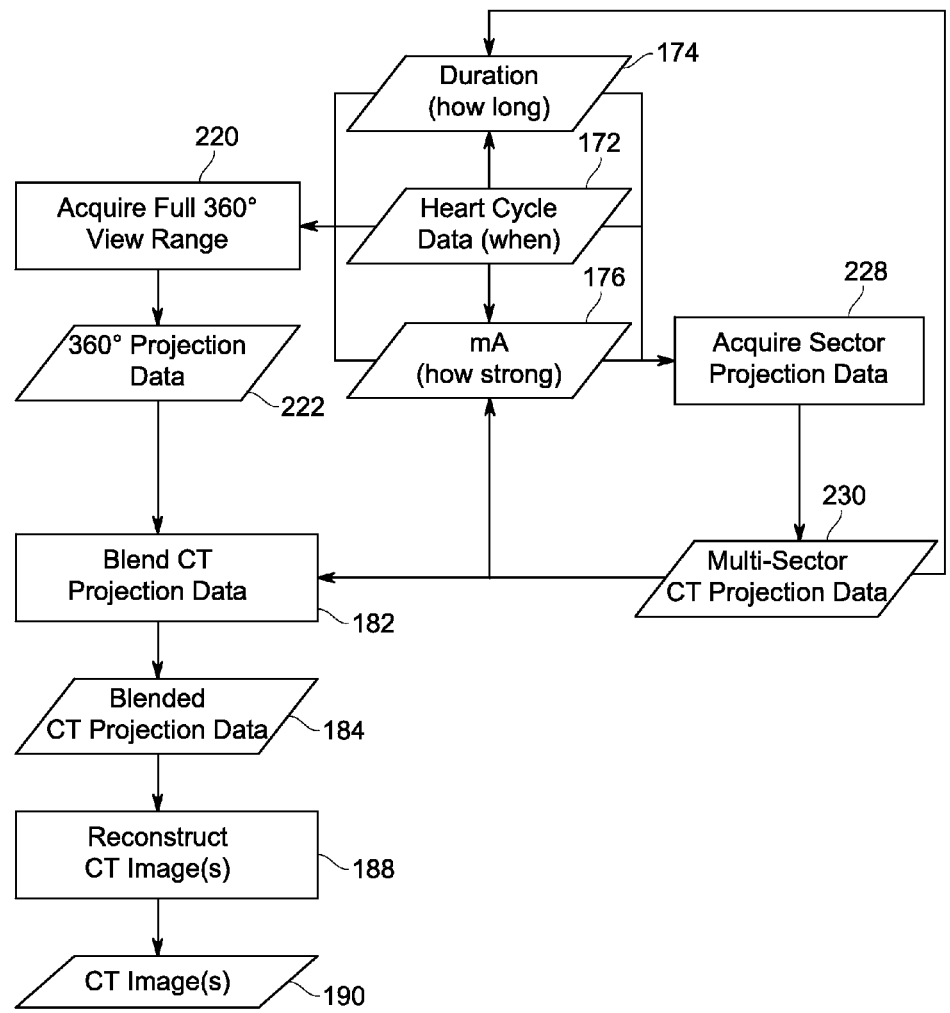
FIG. 9 depicts a process flow diagram of steps performed in a computed tomography data acquisition, in accordance with aspects of the present disclosure.

Turning to FIG. 9, this figure depicts control flow logic describing steps associated with a further implementation of a CT data acquisition as discussed herein, such as with respect to FIG. 8. In this example, an X-ray source 12 is activated (block 220) within a full scan phase window for one heartbeat of a patient undergoing imaging to acquire a 360° projection data set 222. In certain embodiments, the X-ray source 12 is suitable for emitting X-rays in a wide-coverage area (i.e., a coverage area greater than 40 mm), such as a cone-beam. Further, in certain embodiments, the mA used to operate the X-ray source during acquisition of data within window 220 may be relatively low, such as in comparison to subsequent multi-sector data acquisitions.

The activation 220 of the X-ray source 12 may be controlled based on various factors as discussed herein, including, but not limited to, the heart cycle data 172 associated with the patient undergoing imaging. The heart cycle data 172 may be derived from various suitable sources, such as an ECG system, image data, or other systems suitable for determining cardiac motion.

In the depicted example, in addition to the full scan set of 360° projection data 222, one or more sectors of projection data 230 (where a sector of projection data corresponds to less than 180°+α of projection data) are also acquired (block 228) based on the heart cycle data 172. In addition, the multi-sector data acquisitions may be also be controlled for duration and strength (i.e., mA). For example, X-ray pulse duration 174 may be based on one or both of the heart cycle data 172 as well as the multi-sector projection data 230 acquired prior to a present pulse for which the duration is being determined. Similarly, X-ray pulse mA 176 may be based on one or both of the heart cycle data 172 as well as the multi-sector projection data 230 acquired prior to the present pulse for which the mA is being determined. As discussed herein, the various X-ray source parameters such as activation duration, 174, activation time based on heart cycle data 172, and mA 176 may be determined for each X-ray source activation by X-ray controller 26 or system controller 24.

The acquired 360° projection data 222 and multi-sector projection data 230 may be blended or otherwise combined (block 182), as discussed in greater detail below, so as to generate a complete data set 184 with respect to the cardiac phase of interest. In one implementation of the blending 182, a low weight is given to data that is acquired at the very beginning or end of an X-ray pulse to reduce or eliminate discontinuities in the view weighting function. Further, a low weight may also be given to views that were acquired far from the phase-of-interest center-view to increase or maximize temporal resolution. In addition, in certain implementations, the duration of the X-ray pulses may be reduced to reduce or minimize any effective dose penalty realized due to such a weighting scheme. Further, in certain embodiments, if an arrhythmia is detected (e.g., after a particular X-ray pulse, the next R-peak 88 arrives faster than expected), the data acquired for that X-ray pulse can be removed from consideration.

Once the data is blended or otherwise combined, such as with a weighted average approach, the data can be reconstructed (block 188) using a suitable analytic reconstruction algorithm to generate one or more CT images 190 at the phase of interest for review. In one implementation, a view weighting approach utilized in the reconstruction can be adjusted based on the total mAs in each sector of views. Furthermore, unblended super multi-sector data can also be reconstructed, such as using an iterative reconstruction approach. For example, in one implementation, instead of applying determinist weights to blend views to generate a single-scan sonogram, an iterative reconstruction algorithm may be employed to keep weights as a part of a cost function.

Figure 10:
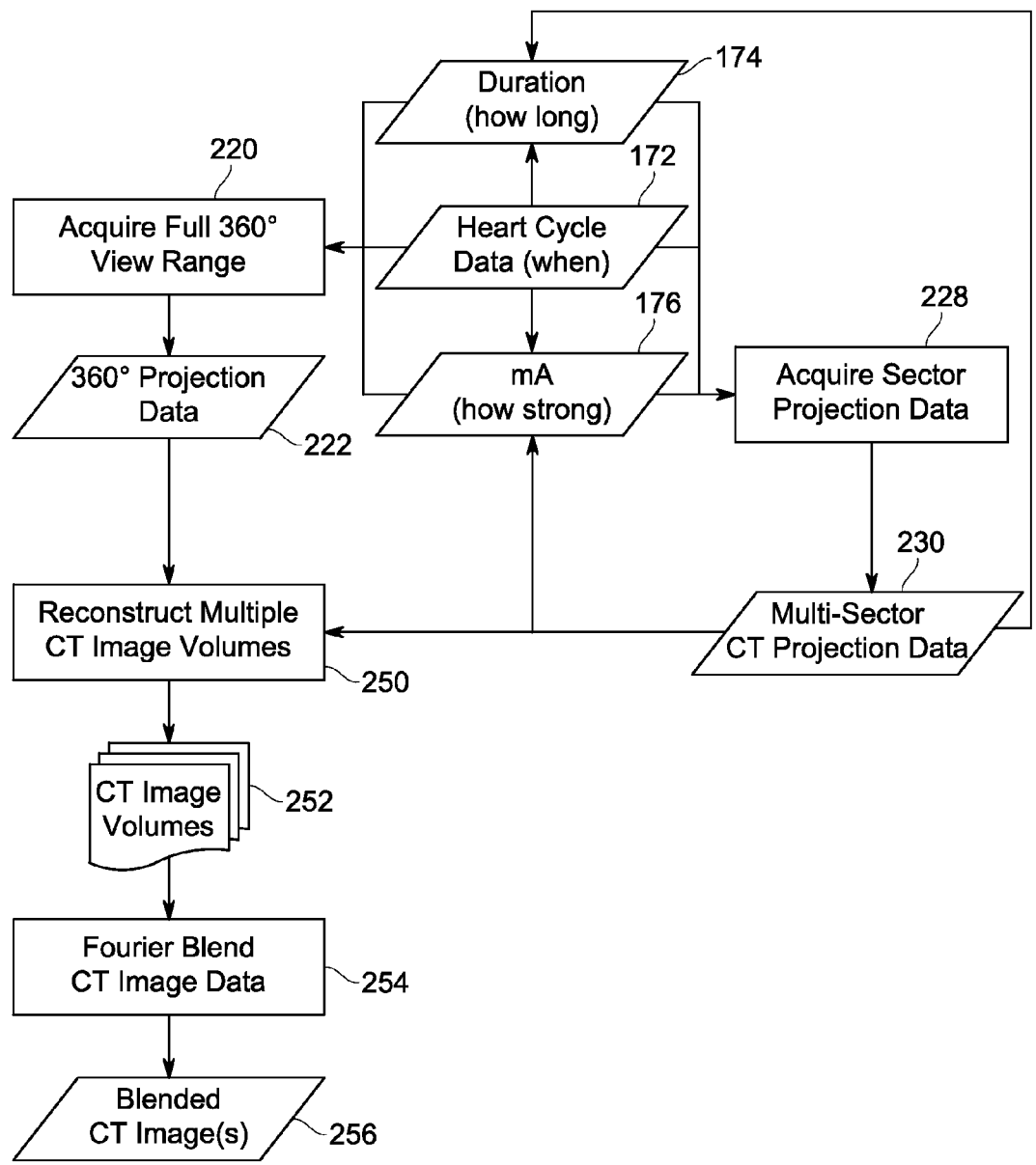
FIG. 10 depicts a process flow diagram of steps performed in a computed tomography data acquisition utilizing Fourier blending, in accordance with aspects of the present disclosure.

The multi sector projection data 230 can also be blended in the Fourier domain rather than in the projection domain. In one such example, Fourier blending is done after image reconstruction, making it a more efficient approach for generating many different images with different weights being applied to the data from different sectors (or heartbeats). Turning to FIG. 10, in one implementation, Fourier blending is done by first reconstructing (block 250) multiple CT image volumes (e.g., multiple stacks of images) 252 and then filtering them before adding them together to generate one or more final or blended images 256. In one such example, the filters are generally substantially uniform in the radial direction in Fourier space and vary in a similar manner to the view weighting in the angular direction. This blending (block 254) can be done retrospectively on a separate image review workstation in order to manually remove the contributions of data from a particular heart cycle if it is found that the data from a particular heart cycle is causing artifacts due to its inconsistency with the other data, provided that the workstation has access to the series of reconstructions (e.g., CT image volumes 252) that are used as input. As an example, 360 degrees of data may be acquired (block 220) in a first heart cycle and 90 degrees of data in each of the two subsequent samples (block 230). Reconstructions may then be performed for each of these datasets (e.g. datasets 222 and 230) wherein full weight is given to the data of the selected sector (discarding any overlapping data) while filling in any missing data in normal conventional manner. In this example, the three reconstructions (CT image volumes 252) may then be blended using Fourier blending (block 254) in order to retrospectively (post-reconstruction) modulate the influence of each in order to produce a good image (image(s) 256).

As with other multi-sector approaches, one factor in the present approach is the natural beat-to-beat variation in the motion of the heart. However, the approach discussed herein may be more robust when such beat-to-beat variation is present since, when there is a beat with a different motion, the varying beat only affects data over a small view range relative to other scan approaches. Further, this limited view range is likely acquired more than once so the impact even within the view range in question is reduced. For example, if the center-views were perfectly distributed in a 16 sector multi-sector acquisition, and 90 degrees of data were acquired at each beat, about 4 contributions would be acquired for every view (i.e., 16 sectors*90°/360°=4).

With respect to the reconstruction process, in one embodiment, a data consistency based selection algorithm may be employed to address inconsistency in the acquired data due to motion variation associated with the patient heartbeats during image acquisition. In particular, a standard CT reconstruction may be based on an assumption that the imaged object or volume is static. Very accurate reconstruction image can be achieved in such contexts, i.e., the error between the measured projections and the re-projected projections (i.e., re-projected from the reconstructed image) is near to zero (with variations possibly being attributable to noise).

However, when the object is moving (or there is motion in the imaged volume), the results may be different as the original static object assumption is not true anymore. Thus, the difference between re-projected projection, Rep, and measured projection, $p_{acq}$, is bigger when the object (e.g., a heart) is moving than when the object is stable. Therefore, the difference between Rep and $p_{acq}$ can be used as a metric for object's motion and used, as discussed below, in a data consistency based reconstruction approach.

For example, in one implementation:

$$p_{acq} = AX_{obj} \tag{1}$$

$$X_{recon} = FBP(p_{acq}) \tag{2}$$

$$Rep = AX_{recon} \tag{3}$$

may be used to characterize the data consistency of projection data acquired at different heartbeats, where $X_{obj}$ is a ground truth image and $X_{recon}$ is a reconstructed image.

The magnitude of the difference between measured projection, $p_{acq}$, and the re-projection, Rep, provides the location and speed of the motion. Based on this metric, all of the views (or heart beats) that have little motion may be retained for reconstruction (or may be given a higher weight in an iterative reconstruction) to reduce artifacts. As noted above, both analytical and iterative algorithms can be used to perform the reconstruction.

Another way a particular sector may be judged in terms of its consistency with other sectors is to perform multiple reconstructions with different blending weights and then to apply an image metric to quantify in some way the degree to which the images are different. For example, one reconstruction could be performed in which the sector of interest is given increased weight in the blending and another reconstruction could be performed in which the sector of interest is discarded (weighted by 0) in the blending. If the resulting reconstructions are similar, then the sector of interest is quite consistent with the other sectors. Conversely, if the resulting reconstructions are significantly different, then the sector of interest can be considered to be inconsistent. If the sector is found to be inconsistent, it can be downweighted or discarded when the final blending occurs. The image metric that is used to measure the degree of consistency can be tailored to focus on certain areas of interest (e.g., the coronary arteries, or some other feature that is of particular clinical interest), provided that such structures are first identified. By way of example, many approaches exist for identifying the locations of the coronary arteries in an automated fashion.

One other approach to measuring data consistency is to skip the reconstruction and compare (via an image metric) the projection data for the sector of interest directly with that of other sectors that acquire the same views. In some cases, filtering of the projection data may be useful prior to this comparison.

As discussed herein multi-sector acquisition as disclosed can provide multiple contributions to every view and allow selection of the most desirable or beneficial contributions, i.e. contributions with best temporal characteristic, such as based on a data consistency metric. For example, in one implementation, views having minimum motion are picked and blended together to produce a minimum motion multi-sector sinogram which can be reconstructed using a suitable analytic reconstruction.

Technical effects include acquisition of multi-sector CT projection data and combination of the acquired sectors of projection data to generate CT images having improved temporal resolution. Technical effects also include combination of multiple sectors of acquired CT projection data based on data consistency to reduce or minimize motion. By way of example, technical effects in a cardiac implementation allow data acquisition from multiple heartbeats and allow flexible selection of the data from the multiple heartbeats so as to improve data consistency and temporal resolution.

This written description uses examples to disclose aspects of the present disclosure, including the best mode, and also to enable any person skilled in the art to practice the present approach, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for adaptively acquiring computed tomography scan data, comprising:
   acquiring heart cycle data for a patient undergoing imaging;
   rotating an X-ray source about the patient;
   activating the X-ray source during two or more heartbeats identified in the heart cycle data, wherein the X-ray source, when activated, emits an X-ray beam that generates projection data for an imaged volume about which the X-ray source is rotating, and wherein one or more of the activations of the X-ray source are adapted in terms of one or more of timing, duration or operating current based on data completeness;
   combining the projection data acquired during the two or more heartbeats based on one or more consistency-based criteria to generate a substantially complete set of projection data; and
   reconstructing the substantially complete set of projection data to generate one or more volumetric images at a cardiac phase of interest.

2. The method of claim 1, wherein the projection data is acquired over an angular range that is less than 180° plus a fan angle of the emitted X-ray beam during each activation of the X-ray source.

3. The method of claim 1, wherein the heart cycle data comprises an electrocardiogram trace.

4. The method of claim 1, wherein activating the X-ray source during the two or more heartbeats comprises activating the X-ray source for different durations for at for at least two of the heartbeats.

5. The method of claim 3, wherein the respective different durations are determined based at least in part upon previously acquired projection data.

6. The method of claim 1, wherein activating the X-ray source during the two or more heartbeats comprises activating the X-ray source using different operating currents for at for at least two of the heartbeats.

7. The method of claim 5, wherein the respective different operating currents are determined based at least in part upon previously acquired projection data.

8. The method of claim 1, wherein the angular range over which the X-ray source is activated during the two of more heartbeats is approximately 90° or less.

9. The method of claim 1, wherein combining the projection data comprises selectively blending acquired projection data based upon the one or more data consistency based criteria.

10. The method of claim 1, comprising activating the X-ray source during an initial heartbeat to acquire projection data over 360° during the initial heartbeat.

11. The method of claim 1, wherein the X-ray beam has a coverage in a z-direction associated with the X-ray source of greater than 40 mm.

12. A computed tomography imaging system, comprising:
    an X-ray source configured to emit X-rays;
    a detector configured to generate data in response to the X-rays emitted by the X-ray source;
    a gantry upon which the X-ray source and detector rotate about an imaging volume;
    an X-ray controller configured to control activation of the X-ray source, wherein the X-ray controller receives as an input heart cycle data and activates the X-ray source during two or more heartbeats identified in the heart cycle data, wherein the X-ray source is adaptively activated over an angular range that is less than 180° plus a fan angle of an emitted X-ray beam during at least activations of the X-ray source of the X-ray source subsequent to an initial activation of the X-ray source; and
    a processing component configured to reconstruct one or more images based on the projection data generated by the detector.

13. The computed tomography imaging system of claim 12, wherein the processing component is further configured to process the projection data generated by the detector based upon one or more data consistency based algorithms and to reconstruct the one or more images using the processed data.

14. The computed tomography imaging system of claim 12, wherein the processing component reconstructs one or more images based on the projection data acquired during each respective activation of the X-ray source such that at least one respective image is reconstructed for each X-ray source activation.

15. The computed tomography imaging system of claim 14, wherein the respective reconstructed images corresponding to the respective X-ray source activations are Fourier blended to generate one or more final images.

16. The computed tomography imaging system of claim 12, wherein the X-ray controller activates the X-ray source for different durations during at least two of the heartbeats.

17. The computed tomography imaging system of claim 12, wherein the X-ray controller activates the X-ray source using different operating currents during at least two of the heartbeats.

18. The computer tomography imaging system of claim 12, wherein the X-ray controller is further configured to activate the X-ray source during an initial heartbeat to acquire data over 360° during the initial heartbeat.

19. A non-transitory, computer-readable medium configured to store one or more routines executable by an imaging system, the routines, when executed, causing acts to be performed comprising:
- acquiring heart cycle data;
- rotating an X-ray source about an imaging volume;
- activating the X-ray source during two or more heartbeats identified in the heart cycle data, wherein the X-ray source, when activated, emits an X-ray beam that generates projection data for the imaged volume, and wherein one or more of the activations of the X-ray source are adapted in terms of one or more of timing, duration or operating current based on data completeness;
- combining the projection data acquired during the two or more heartbeats based on one or more consistency-based criteria; and
- reconstructing the combined projection data to generate one or more volumetric images.

20. The non-transitory, computer-readable medium of claim 19, wherein activating the X-ray source during the two or more heartbeats comprises activating the X-ray source for different durations for at for at least two of the heartbeats.

21. The non-transitory, computer-readable medium of claim 19, wherein activating the X-ray source during the two or more heartbeats comprises activating the X-ray source using different operating currents for at for at least two of the heartbeats.

22. The non-transitory, computer-readable medium of claim 19, wherein the one or more routines further comprise a routine, which, when executed causes an act to be performed comprising:
- activating the X-ray source during an initial heartbeat to acquire projection data over 360° during the initial heartbeat.

* * * * *